United States Patent
Szelenyi et al.

(12)

(10) Patent No.: US 7,022,687 B1
(45) Date of Patent: Apr. 4, 2006

(54) COMBINATION OF LOTEPREDNOL AND ANTIHISTAMINES

(75) Inventors: Istvan Szelenyi, Schwaig (DE); Degenhard Marx, Radebeul (DE); Sabine Heer, Radebeul (DE); Juergen Engel, Alzenau (DE)

(73) Assignee: Asta Medica AG, Dresden (DE)

( * ) Notice: Subject to any disclaimer, the term of this patent is extended or adjusted under 35 U.S.C. 154(b) by 301 days.

(21) Appl. No.: 10/089,436

(22) PCT Filed: Sep. 26, 2000

(86) PCT No.: PCT/EP00/09391

§ 371 (c)(1),
(2), (4) Date: Jul. 23, 2002

(87) PCT Pub. No.: WO01/22955

PCT Pub. Date: Apr. 5, 2001

(30) Foreign Application Priority Data

Sep. 30, 1999 (DE) ........................ 199 47 234

(51) Int. Cl.
*A61K 31/56* (2006.01)
*A61K 31/55* (2006.01)
*A61K 31/47* (2006.01)

(52) U.S. Cl. .................. 514/179; 514/217.05; 514/330
(58) Field of Classification Search .................. 514/179, 514/217.05, 330
See application file for complete search history.

(56) References Cited

U.S. PATENT DOCUMENTS 4,710,495 A 12/1987 Bodor
4,996,335 A 2/1991 Bodor

FOREIGN PATENT DOCUMENTS

EP 0 709 099 5/1996
WO WO 97/01337 1/1997

OTHER PUBLICATIONS

Friedlaender, Current Opinion in Ophthalmology 1998, 9/4 54–58.*
Isaac, Lancet, Worldwide variation in prevalence of symptoms of asthma, allergic rhinoconjunctivitis, and atopic eczema, vol. 351, pp. 1225–1332, Aug. 25, 1998.
I. Annesi–Maesano et al., Revue Francaise d'Allergologie, "La rhinite de l'adolescent Resultats de l'enquete ISAAG" vol. 38, pp. 283–289, 1998.
Medline, E. Norman et al., European Journal of Allergy, "Prevalence and incidence of asthma and rhinoconjunctivitis in Swedish teenagers," vol. 53, pp. 28–35, 1998, abstract.

* cited by examiner

Primary Examiner—Rebecca Cook
(74) Attorney, Agent, or Firm—Burns, Doane, Swecker & Mathis, L.L.P.

(57) ABSTRACT

The present invention relates to a novel combination of a soft steroid, in particular loteprednol, and at least one antihistamine, such as, for example, azelastine and/or levocabastine, for simultaneous, sequential or separate administration in the local treatment of allergies and airway disorders, for example of allergic rhinitis (rhinoconjunctivitis).

12 Claims, No Drawings

COMBINATION OF LOTEPREDNOL AND ANTIHISTAMINES

This is a 371 of PCT/EP00/09391 filed Sep. 26, 2000.

The present invention relates to a novel combination of a soft steroid, in particular loteprednol, and at least one antihistamine, such as, for example, azelastine and/or levocabastine, for simultaneous, sequential or separate administration in the local treatment of allergies and airway disorders, for example of allergic rhinitis or rhinoconjunctivitis.

BACKGROUND OF THE INVENTION

The number of allergic disorders is increasing greatly worldwide. Studies have shown that on average 7.5% of all children and adolescents worldwide suffer from rhinoconjunctivitis (hay fever combined with an ocular symptomatology) (Worldwide variation in prevalence of symptoms of asthma, allergic rhinoconjunctivitis and atopic eczema: ISAAC, Lancet, 351, 1225–1332, 1998). In West European countries, the prevalence, at about 14%, is markedly higher (Annesi-Maesano I. and Oryszczyn MP.: Rhinitis in adolescents, Results of the ISAAC survey, Revue Francaise d'Allergologie et d'Immunologie Clinique, 38, 283–289, 1998; Norman E., Nystrom L, Jonsson E and Stjernberg N: Prevalence and incidence of asthma and rhinoconjunctivitis in Swedish teenagers, European Journal of Allergy and Clinical Immunology, 53, 28–35, 1998). Despite intensive research activity, the pathogenesis of rhinoconjunctivitis has still not been completely clarified. Even if marked advances in the medical treatment of this disorder have been achieved in the past years, the therapy is still not satisfactory. The acute symptoms (itching, reddening, swelling, rhinorrhea and lacrimation) of rhinoconjunctivitis can be readily controlled, inter alia with the aid of antihistamines. However, they barely have a therapeutically relevant influence on the inflammation which underlies the disorder and is always progressive. Often, allergic rhinitis or rhinoconjunctivitis is regarded both by patients and by the physician as a trivial disorder and accordingly is only inadequately treated. As a result, however, a so-called change of stage can occur, i.e. bronchial asthma, which is to be taken very seriously, develops from the relatively harmless rhinitis. For this reason, it is indispensable to treat even allergic rhinoconjunctivitis adequately and intensively. Only then can the patients live symptom-free and only then can a change of stage, which under certain circumstances is life-threatening, be prevented.

Frequently, it cannot be established by the treating physician in borderline cases with absolute certainty whether "only" rhinoconjunctivitis is still present or whether an airway disorder, such as bronchial asthma, is already present. It is advantageous if the combination according to the invention can also be employed for the treatment of disorders of the upper and lower airways.

At the present time, the corticosteroids are most effectively able to control the inflammation underlying the rhinoconjunctivitis. Many patients, but also physicians, however, do not employ these medicaments at all or only very hesitantly, usually only in a late phase of the disorder, because of their possible systemic side effects (e.g. slow-down in growth, osteoporosis).

Loteprednol belongs to the so-called "soft" steroids. Unlike other corticosteroids, which are usually only broken down in the liver to give pharmacodynamically inactive metabolites, in the case of the soft steroids the metabolic inactivation partly already takes place at the site of their administration (intranasal, ocular or intrapulmonary). As a result of this partial local metabolization, no or only very little pharmacodynamically active substance reaches the systemic blood circulation, so that the steroid-specific side effects virtually do not have to be reckoned with. Loteprednol is already licensed for the therapy of allergic conjunctivitis and uveitis.

Antihistamines are employed in the acute phase of allergic rhinoconjunctivitis for the alleviation of the often irritating symptoms. The topical application of these medicaments is particularly advantageous, as high local concentrations of the active compound can be broken down in this way without having to reckon with appreciable side effects. At the current time, two locally administrable antihistamines, azelastine and levocabastine, are on the market. Both are highly efficacious and very highly tolerable.

Surprisingly, it has now been found that the novel combination of a soft steroid and at least one antihistamine is advantageous in the treatment of allergies and/or airway disorders by topical administration. Administration can in this case be carried out simultaneously, sequentially or separately. The invention serves to improve the therapy of allergic rhinitis (rhinoconjunctivitis). The antihistamine provides for the rapid elimination of the acute symptoms (e.g. reddening, itching, swelling). Using the corticosteroid contained in the combination, the inflammation underlying the condition can be successfully controlled.

According to one embodiment of the invention, loteprednol and its pharmaceutically acceptable esters, in particular loteprednol etabonate, is a particularly suitable soft steroid. The preparation of loteprednol and loteprednol etabonate is described, for example, in German Patent No. DE 31 26 732, the corresponding U.S. Pat. No. 4,996,335 and the corresponding Japanese Patent No. JP-89 011 037.

Further suitable soft steroids according to the invention are described, for example, in German Patent No. 37 86 174, the corresponding European Patent No. EP 0 334 853 and the corresponding U.S. Pat. No. 4,710,495.

Azelastine and levocabastine can also be used in the form of the pharmaceutically tolerable salts. The hydrochlorides, for example, are preferred.

By means of the topical administration of the components (steroid and antihistamine), therapeutically efficacious concentrations can be achieved even at low doses. The combined administration of both substances (antihistamine+loteprednol) makes possible the control of the troublesome early-phase reactions such as itching, rhinorrhea by the antihistamine and the progress of the inflammation by the loteprednol. Moreover, the danger of the occurrence of undesired effects is thereby reduced to a minimum and better compliance of the patients is thus to be expected.

The present invention describes a novel combination, in which a soft steroid (preferably loteprednol) and an antihistamine (preferably azelastine and/or levocabastine) are given topically (intranasally or intraocularly) simultaneously, one after the other as individual substances or as a fixed combination. As a result of this combination, not only a rapid onset of action occurs but also a high therapeutic efficacy is achieved, which is accompanied by a strong antiinflammatory action. In one advantageous embodiment, the active components of this combination are present in the form of a fixed combination, owing to which the administration is simpler for the patients, since both active compounds are contained in one and the same container.

According to a further embodiment of the invention, the antihistamine can also be administered orally.

The intended dosage is carried out twice daily, the individual dose of the soft steroid (loteprednol) being between 10 and 500 µg, preferably 50 and 200 µg. The dose of antihistamine is 50–500 µg, preferably 100–200 µg. The actual dose depends on the general condition of the patients (age, weight, etc.) and the degree of severity of the disorder.

The following pharmacological investigation was carried out in order to support the invention described.

In vitro, investigations on the influencing of the release of the proinflammatory cytokine TNFα in human blood of various donors diluted 1:5 were carried out. The stimulation was effected using lipopolysaccharide (LPS) from Salmonella abortus equi (10 µg/ml) over the course of 24 h at 37° C. and 5% $CO_2$ in an incubator. The TNFα release was determined using an ELISA, based on antibodies from Pharmingen. The results were indicated as the percentage inhibition of the LPS-induced TNFα release and are shown in Table 1.

TABLE 1

| Active compound | Concentration (µmol/l) | Inhibition of TNFα release |
| --- | --- | --- |
| Azelastine | 10 | 2% |
| Loteprednol | 0.001 | 1% |
|  | 0.01 | 2% |
|  | 0.03 | 8% |
| Azelastine + loteprednol | 10 + 0.001 | 12%* |
|  | 10 + 0.01 | 18%* |
|  | 10 + 0.03 | 22%* |

*significant (p < 0.05)

If the antihistamine azelastine or the soft steroid loteprednol is administered alone, the LPS-induced TNFα release remains virtually unchanged. In the presence of azelastine (10 µmol/l) the TNFα release is inhibited to an increased extent by loteprednol in a concentration-dependent manner.

In vivo investigations were carried out on young domestic pigs actively sensitized with an antigen (extract from Ascaris suum). Three weeks later, they were exposed to allergen challenge, which was carried out by intranasal instillation of the Ascaris extract. This local intranasal allergen challenge leads to a very great increase in the nasal secretion (rhinorrhea). The amount of secretion was determined gravimetrically. The results are compiled in Table 2.

TABLE 2

| Active compound | Dose in µg/nostril | Inhibition of nasal secretion | Number of animals |
| --- | --- | --- | --- |
| Azelastine | 10 | 15% | 5 |
| Loteprednol | 20 | 8% | 5 |
| Azelastine + loteprednol | 10 + 20 | 48%* | 5 |

*significant (p < 0.05)

If the antihistamine azelastine or the soft steroid loteprednol is used at the dosages 10 or 20 µg/nostril, only marginal inhibition of the allergically induced nasal hypersecretion occurs. If both active compounds are given at the same time, however, the rhinorrhoea is (significantly) reduced by 48%.

Various pharmaceutical formulations, e.g. nasal sprays, nasal drops and eye drops, are suitable for topical application.

The present invention describes a combination in which a soft steroid, e.g. loteprednol, and an antihistamine, e.g. azelastine and/or levocabastine, are administered simultaneously, one after the other as individual substances or as a fixed combination.

On account of the water solubility of the active compound azelastine hydrochloride, formulations containing this active compound can preferably be formulated as solutions. Loteprednol etabonate, however, is virtually water-insoluble and is therefore formulated as an aqueous suspension. In a formulation in which both active compounds are combined, azelastine hydrochloride is accordingly present dissolved in water and loteprednol etabonate suspended in water.

In addition to the active constituents antihistamine, e.g. azelastine hydrochloride, and soft steroid, e.g. loteprednol etabonate, the pharmaceutical preparations according to the invention can contain further constituents such as preservatives, stabilizers, isotonicizing agents, thickeners, suspension stabilizers, excipients for pH adjustment, buffer systems and wetting agents.

Examples of suitable preservatives are: benzalkonium chloride, chlorobutanol, thiomersal, methylparaben, propylparaben, sorbic acid and its salts, sodium edetate, phenylethyl alcohol, chlorhexidine hydro-chloride acetate and digluconate, cetylpyridinium chloride and bromide, chlorocresol, phenylmercury acetate, phenylmercury nitrate, phenylmercury borate, phenoxyethanol.

For preservation, the combination of sodium edetate and benzalkonium chloride is preferably used. Sodium edetate is employed here in concentrations of 0.05–0.1% and benzalkonium chloride in concentrations of 0.005–0.05%. The combination of sodium edetate, benzalkonium chloride and phenylethyl alcohol is also preferably employed.

Suitable excipients for the adjustment of the isotonicity of the formulations are, for example: sodium chloride, potassium chloride, mannitol, glucose, sorbitol, glycerol, propylene glycol. In general, these excipients are employed in concentrations from 0.1 to 10%.

The formulations of the invention can also include suitable buffer systems or other excipients for pH adjustment in order to establish and maintain a pH of the order of magnitude of 4–8, preferably of 5 to 7.5. Suitable buffer systems are citrate, phosphate, trometham ol glycine, borate, acetate. These buffer systems can be prepared from substances such as, citric acid, monosodium phosphate, disodium phosphate, glycine, boric acid, sodium tetraborate, acetic acid, sodium acetate. Further excipients can also be used for pH adjustment, such as hydrochloric acid or sodium hydroxide.

In order to prepare a stable aqueous suspension containing the water-insoluble active compound loteprednol etabonate, suitable suspension stabilizers and suitable wetting agents are furthermore necessary in order to disperse and to stabilize the suspended active compound in a suitable manner.

Suitable suspension stabilizers are water-soluble or partly water-soluble polymers: these include, for example, methylcellulose (MC), sodium carboxymethyl-cellulose (Na-CMC), hydroxypropylmethylcellulose (HPMC) polyvinyl alcohol (PVAL [sic]), polyvinylpyrrolidone (PVP), polyacrylic acid, polyacrylamide, gellan gum (Gelrite®) hydrated alumina (Unemul®) dextrins, cyclodextrins, and mixtures of Microcrystalline cellulose and sodium carboxymethylcellulose (Avicel RC 501®, Avicel RC 581®, Avicel RC 591®, Avicel CL 611®). These substances can simultaneously serve as thickeners in order to increase the viscosity and thereby to prolong the contact of the active compounds with the tissue at the application site.

Suitable wetting agents for the formulations are: benzalkonium chloride, cetylpyridinium chloride, tyloxapol, various polysorbates (Tween®), and further polyethoxylated substances and poloxamers.

EXAMPLES

The following examples illustrate the invention without restricting it.

Example 1

Nasal spray containing azelastine hydrochloride (0.1%)

| | |
|---|---|
| Azelastine hydrochloride | 0.1000 g |
| Hydroxypropylmethylcellulose | 0.1000 g |
| Sodium edetate | 0.0500 g |
| Benzalkonium chloride | 0.0125 g |
| Sodium hydroxyde | q.s. ph 6.0 |
| Sorbitol solution 70% | 6.6666 g |
| Purified water | to 100 ml |

Preparation of the solution

Introduce about 45 kg of purified water into a suitable stirrer container. Add the active compound, hydroxypropylmethylcellulose, sodium edetate, benzalkonium chloride and sorbitol solution to this in succession and dissolve with stirring. Make up the resulting solution to a volume of 49.5 liters with purified water. Adjust the pH of the solution to pH 6.0 using 1N sodium hydroxide solution. Make up to the final volume of 50.0 liters using purified water and Stir. Filter the solution through a suitable filter and dispense into bottles which are then provided with a suitable nasal spray pump.

Example 2

Nasal spray suspension containing loteprednol etabonate (1%)

| | |
|---|---|
| Loteprednol etabonate | 1.0000 g |
| Avicel RC 591 | 1.1000 g |
| Polysorbate 80 | 0.1000 g |
| Sorbitol solution 70% | 6.0000 g |
| Sodium edetate | 0.0500 g |
| Benzalkonium chloride | 0.0200 g |
| Purified water | to 100 ml |

Preparation

Introduce 45 kg of purified water into a suitable stirrer container with a homogenization device and homogenize Avicel RC 591 therein at high speed. Then dissolve the substances polysorbate 80, sorbitol solution, sodium edetate and benzalkonium chloride in succession with stirring. Then homogenize the active compound loteprednol etabonate at high speed until a uniform suspension is formed. Then make up to the final volume of 50 liters with purified water and homogenize further. Then evacuate the suspension in order to remove the resulting air bubbles. The resulting suspension is then dispensed into bottles which are then provided with a suitable nasal spray pump.

Example 3

Nasal spray containing loteprednol etabonate (1%, suspended) and azelastine hydrochloride (0.1%, dissolved)

| | |
|---|---|
| Loteprednol etabonate | 1.0000 g |
| Azelastine hydrochloride | 0.1000 g |
| Avicel RC 591 | 1.1000 g |
| Polysorbate 80 | 0.1000 g |
| Sorbitol solution 70% | 6.0000 g |
| Sodium edetate | 0.0500 g |
| Benzalkonium chloride | 0.0200 g |
| Purified water | to 100 ml |

Preparation

Introduce 45 kg of purified water into a suitable stirrer container with a homogenization device and homogenize Avicel RC 591 therein at high speed. Then dissolve the active compound azelastine hydrochloride and the excipients polysorbate 80, sorbitol solution, sodium edetate and benzalkonium chloride in succession with stirring.

Then homogenize the active compound loteprednol etabonate at high speed until a uniform suspension is formed. Then make up to the final volume of 50 liters with purified water and homogenize further. Then evacuate the suspension in order to remove the resulting air bubbles.

The resulting suspension is then dispensed into bottles which are then provided with a suitable nasal spray pump.

What is claimed is:

1. A pharmaceutical composition comprising an effective amount of loteprednol or a pharmaceutically acceptable ester thereof and an effective amount of azelastine.

2. The composition according to claim 1, wherein the azelastine is administrable nasally or ocularly.

3. The composition according to claim 1, wherein the pharmaceutically tolerable ester is loteprednol etabonate.

4. A method for the treatment of one or more allergic disorders selected from the group consisting of allergic rhinitis and allergic conjunctivitis comprising administering to a person in need thereof, an effective amount of loteprednol or a pharmaceutically acceptable ester thereof and an effective amount of intranasally or intraocularly administrable azelastine optionally together with customary excipients or vehicles, for simultaneous, sequential or separate administration.

5. A method for the treatment and prophylaxis of one or more allergic disorders selected from the group consisting of allergic rhinitis and allergic conjunctivitis, comprising administering to a person in need thereof, an effective amount of loteprednol and an effective amount of azelastine, wherein the loteprednol or a pharmaceutically acceptable ester thereof and the azelastine is administered simultaneously, sequentially or separately, optionally together with customary excipients or vehicles.

6. The method according to claim 5, wherein the loteprednol is administered as an inhalable liquid preparation.

7. The method according to claim 5, wherein the azelastine is administered orally.

8. A method for the treatment of one or more allergic disorders selected from the group consisting of allergic rhinitis and allergic conjunctivitis comprising administering to a patient in need thereof, a combination of an effective amount of loteprednol or a pharmaceutically acceptable ester thereof and an effective amount of azelastine for simultaneous, sequential or separate administration.

9. The composition according to claim 1, wherein the daily dose of loteprednol is between 10 and 500 μg and the daily does of azelastine is between 50 and 500 μg.

10. The method according to any one of claims 4, 6 or 8 wherein the daily dose of loteprednol is between 10 and 500 μg, and the daily dose of azelastine is between 50 and 500 μg.

11. The method of claim 9, wherein the daily dose of loteprednol is between 50 and 200 μg and the daily does of azelastine is between 100 and 200 μg.

12. The method of claim 10, wherein the daily dose of loteprednol is between 50 and 200 μg and the daily does of azelastine is between 100 and 200 μg.

* * * * *